US012599369B2

(12) United States Patent
Zhou et al.

(10) Patent No.: US 12,599,369 B2
(45) Date of Patent: Apr. 14, 2026

(54) ULTRASOUND METHODS AND SYSTEMS FOR MEASURING PHYSIOLOGICAL PROPERTIES

(71) Applicant: FUJIFILM SonoSite, Inc., Bothell, WA (US)

(72) Inventors: Yong Zhou, Woodinville, WA (US); Jean Tsou, Seattle, WA (US)

(73) Assignee: FUJIFILM SonoSite, Inc., Bothell, WA (US)

( * ) Notice: Subject to any disclaimer, the term of this patent is extended or adjusted under 35 U.S.C. 154(b) by 28 days.

(21) Appl. No.: 18/593,440

(22) Filed: Mar. 1, 2024

(65) Prior Publication Data

US 2025/0275755 A1    Sep. 4, 2025

(51) Int. Cl.
*A61B 8/00* (2006.01)
*A61B 8/06* (2006.01)

(52) U.S. Cl.
CPC .............. *A61B 8/5223* (2013.01); *A61B 8/06* (2013.01)

(58) Field of Classification Search
CPC ........... A61B 8/5223; A61B 8/06; A61B 8/04; A61B 8/0891; A61B 8/486; A61B 8/5207; A61B 8/488
See application file for complete search history.

(56) References Cited

U.S. PATENT DOCUMENTS 6,176,832 B1 * 1/2001 Habu ................... A61B 5/0285
                                                            600/490
2019/0000415 A1 * 1/2019 Anand ................ G01S 7/52066

* cited by examiner

*Primary Examiner* — Bo Joseph Peng

(74) *Attorney, Agent, or Firm* — Colby Nipper PLLC

(57) ABSTRACT

Ultrasound methods and systems for measuring physiological properties are disclosed. The ultrasound methods and systems measure one or more characteristics of a vessel, such as vessel-wall displacement over time or blood-flow velocity over time, based on a pulse wave propagating through the vessel. In aspects, the characteristics are measured at two locations of the same vessel with a known distance between the two locations. A time shift between the measured characteristics at the two locations is calculated and used, along with the known distance, to determine one or more physiological properties, such as pulse-wave velocity or blood pressure. These physiological properties can be measured without the assistance of ECG data.

20 Claims, 13 Drawing Sheets

100

200

300

800

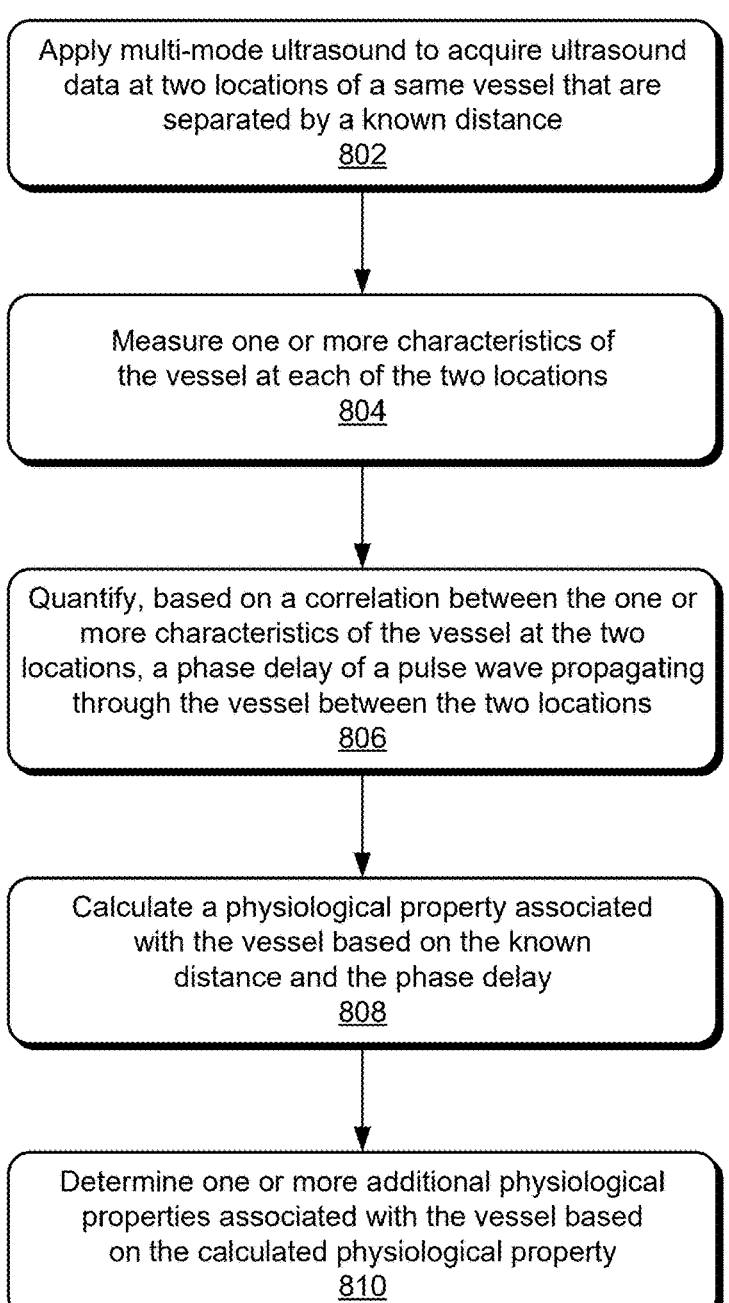

Apply multi-mode ultrasound to acquire ultrasound
data at two locations of a same vessel that are
separated by a known distance
802

Measure one or more characteristics of
the vessel at each of the two locations
804

Quantify, based on a correlation between the one or
more characteristics of the vessel at the two
locations, a phase delay of a pulse wave propagating
through the vessel between the two locations
806

Calculate a physiological property associated
with the vessel based on the known
distance and the phase delay
808

Determine one or more additional physiological
properties associated with the vessel based
on the calculated physiological property
810

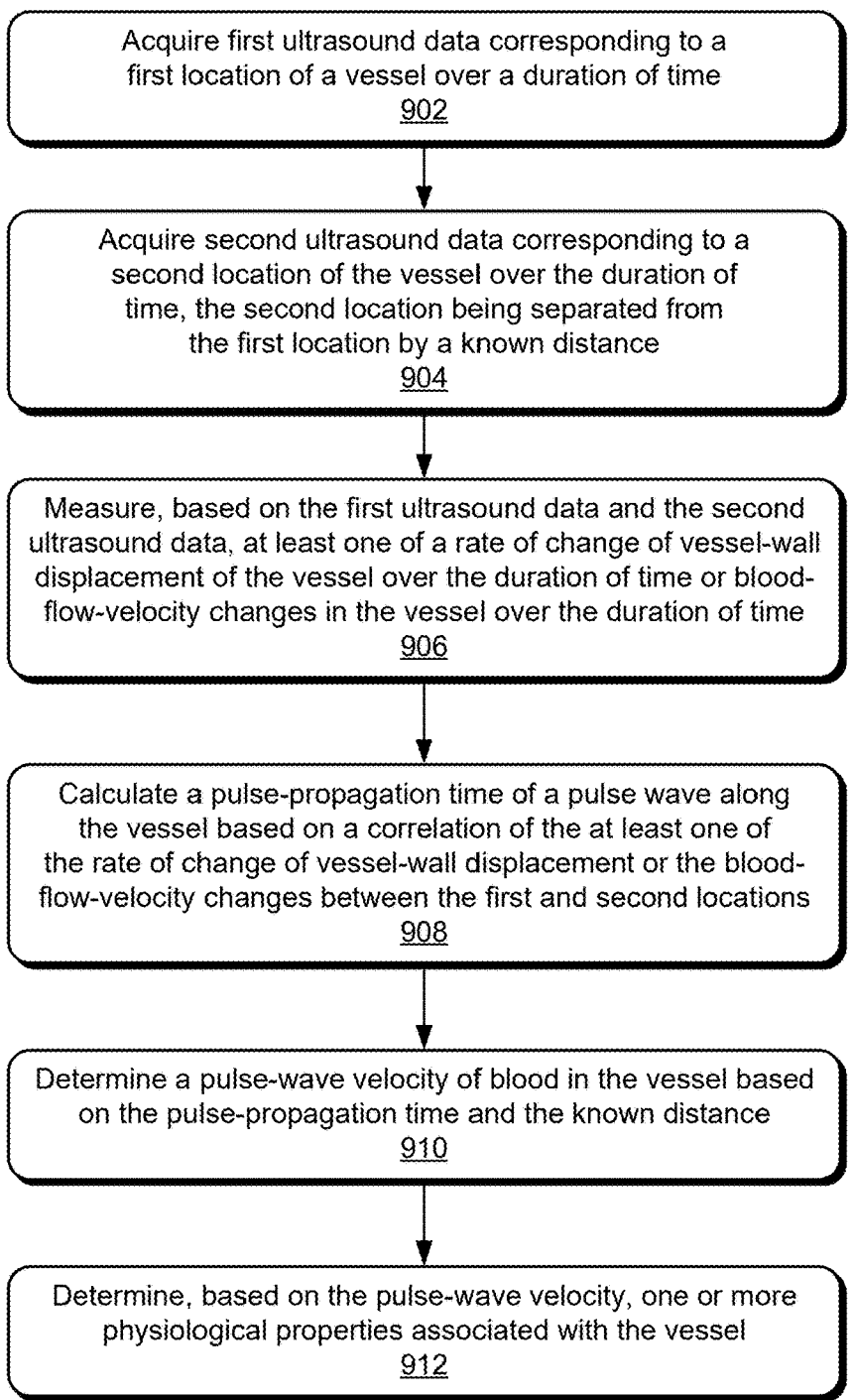

Acquire first ultrasound data corresponding to a
first location of a vessel over a duration of time
902

Acquire second ultrasound data corresponding to a
second location of the vessel over the duration of
time, the second location being separated from
the first location by a known distance
904

Measure, based on the first ultrasound data and the second
ultrasound data, at least one of a rate of change of vessel-wall
displacement of the vessel over the duration of time or blood-
flow-velocity changes in the vessel over the duration of time
906

Calculate a pulse-propagation time of a pulse wave along
the vessel based on a correlation of the at least one of
the rate of change of vessel-wall displacement or the blood-
flow-velocity changes between the first and second locations
908

Determine a pulse-wave velocity of blood in the vessel based
on the pulse-propagation time and the known distance
910

Determine, based on the pulse-wave velocity, one or more
physiological properties associated with the vessel
912

ULTRASOUND METHODS AND SYSTEMS FOR MEASURING PHYSIOLOGICAL PROPERTIES

BACKGROUND

Ultrasound is widely used to image human cardiac anatomy and detect cardiac functions, such as ejection fraction and left ventricle outflow traction (LVOT). Conventional ultrasound lacks the capability, however, to accurately measure other physiological properties, such as pulse-wave velocity (PWV) and blood pressure (BP). Some of the challenges of measuring pulse-wave velocity include, for example, the fact that pulse-wave velocity (e.g., the speed of a pulse wave propagation through the blood stream) is extremely fast, which causes conventional systems to be unable to directly measure the pulse wave. Blood pressure is also challenging to measure with ultrasound because blood pressure depends on several physiological parameters including, for example, vessel diameter, vessel stiffness, cardiac output pressure, and distance between the heart and a measurement location. Even with the assistance of an electrocardiogram (ECG) to monitor a heart cycle, measuring PWV is difficult due to the long distance between the heart and the measurement location.

SUMMARY

Ultrasound methods and systems for measuring physiological properties are disclosed. The ultrasound methods and systems can measure one or more characteristics of a vessel, such as vessel-wall displacement over time or blood-flow velocity over time, based on a pulse wave propagating through the vessel. In aspects, the characteristics are measured at two locations of the same vessel with a known distance between the two locations. A time shift between the measured characteristics at the two locations is calculated and used, along with the known distance, to determine one or more physiological properties, such as pulse-wave velocity and/or blood pressure. These physiological properties can be measured without the assistance of ECG data.

In some aspects, an ultrasound system is disclosed. The ultrasound system can include an ultrasound scanner to generate ultrasound data based on reflections of ultrasound signals transmitted by the ultrasound scanner at an anatomy. The ultrasound scanner is also configured to acquire the ultrasound data at two locations of a same vessel that are separated by a distance, and the ultrasound data is acquired at the two locations within a time interval. The ultrasound system also includes one or more processors and one or more computer-readable storage media having instructions stored thereon that, responsive to execution by the one or more processors, cause the one or more processors to: determine one or more characteristics of the vessel at each of the two locations using the ultrasound data; determine, based on a correlation between the one or more characteristics of the vessel at the two locations, a phase delay of a pulse wave propagating through the vessel between the two locations; and determine a physiological property associated with the vessel based on the one or more characteristics and the known distance.

In aspects, a method is disclosed. The method includes acquiring ultrasound data at two locations of a same vessel that are separated by a known distance, the ultrasound data acquired at the two locations within a time interval. The method also includes determining one or more characteristics of the vessel at each of the two locations using the ultrasound data. In addition, the method includes determining, based on a correlation between the one or more characteristics of the vessel at the two locations, a phase delay of a pulse wave propagating through the vessel between the two locations. The method further includes determining a physiological property associated with the vessel based on the one or more characteristics and the known distance.

BRIEF DESCRIPTION OF THE DRAWINGS

The appended drawings illustrate examples and are, therefore, exemplary embodiments and not considered to be limiting in scope. Throughout the drawings, the same numbers are used to reference like features and components.

FIG. 8 depicts a method for using ultrasound to measure physiological properties.

FIG. 9 depicts a method for measuring physiological properties using ultrasound.

DETAILED DESCRIPTION

Figure 1:
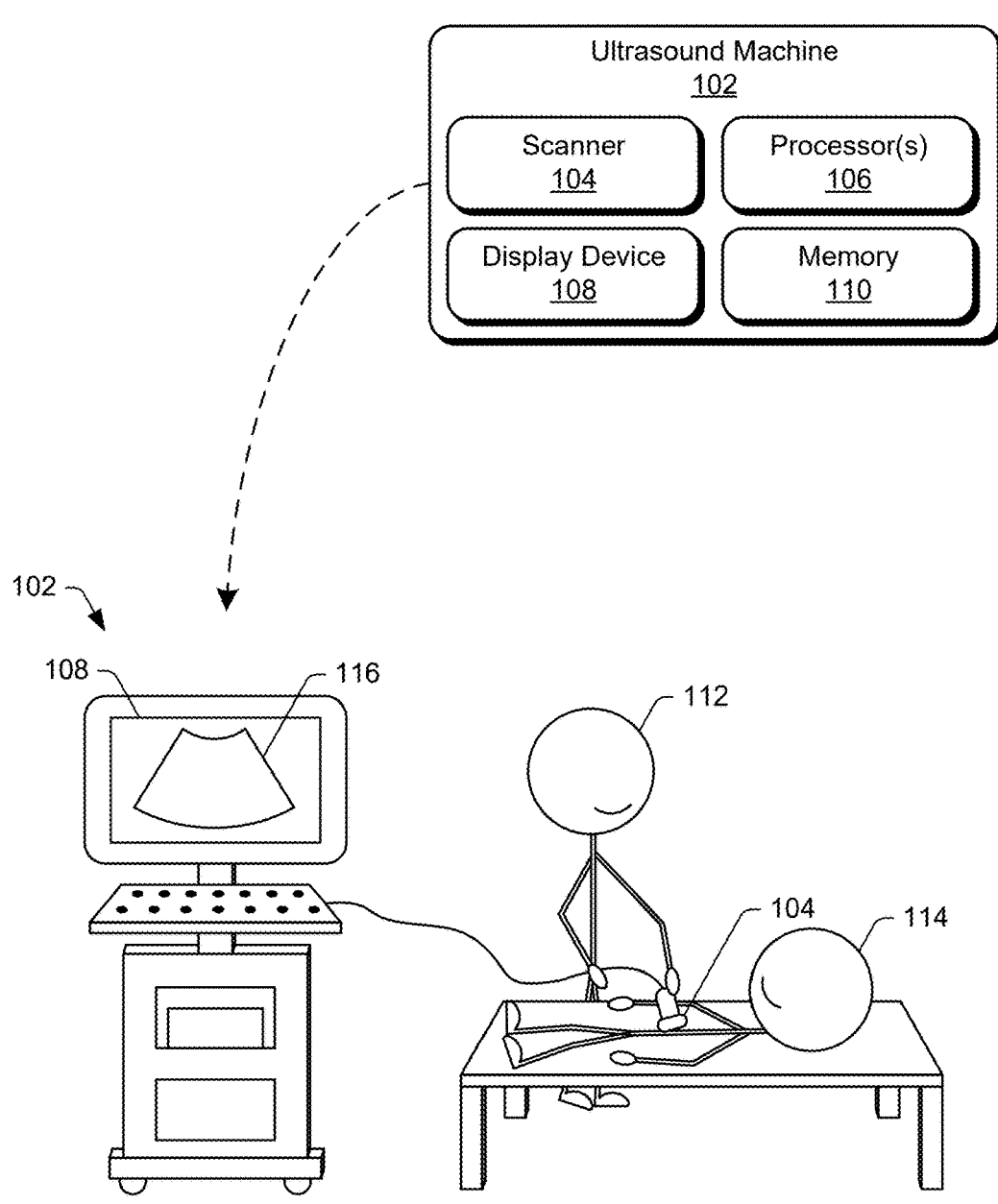
FIG. 1 illustrates an example environment for an ultrasound system having an ultrasound scanner, in accordance with one or more implementations.

Disclosed herein are ultrasound methods and systems for measuring physiological properties. These techniques and systems provide increased accuracy compared to conventional techniques used to measure physiological properties. The techniques and systems disclosed herein use ultrasound, without the assistance of an electrocardiogram (ECG), to measure such physiological properties of a subject, which reduces errors in the calculations that are typically due to estimations of the distance between the heart and the actual location being measured. Example physiological properties being measured include pulse-wave velocity and blood pressure.

Pulse-wave velocity (PWV) is the speed at which pressure waves move through the circulatory system, such as an artery or a combined length of arteries or blood vessels. PWV is an independent predictor of cardiovascular risk. Assessment of PWV can be performed noninvasively by measuring the carotid and femoral pulse pressures and the time delay between the two. PWV increases with increased arterial stiffness. In addition, PWV is a reliable prognostic marker for cardiovascular morbidity and mortality. Research shows that hypertension contributes to an increase in age-related arterial stiffening. While blood pressure (BP) is a valuable first-level indicator of hypertension, PWV provides further detail. The mean values of pulse-wave velocity for 20-29 year olds is 5.8±0.7 meters per second (m/s) and for 40-49 years is 7.1±0.9 m/s. Because BP is one of the most important contributing factors to PWV, measuring the pulse-wave velocity (PWV) is generally considered to be a promising technique for continuous noninvasive measurements of BP. However, conventional methods to measure PWV are not very accurate or convenient. For example, to measure PWV conventionally, an ECG-aided ultrasound method was used. However, in such a method, the distance between the heart and the measurement location is estimated and can lead to a huge error.

The techniques and systems disclosed herein use only an ultrasound system (without using ECG) to measure PWV and BP. Using these techniques, distance estimation errors are reduced or eliminated, resulting in higher accuracy of the measurement compared to conventional techniques. The pulse wave is a pressure wave initialized by the heart and propagates along the vessels, which leads to two consequences: first, the vessel wall is compressed and the compression ratio depends on the vessel wall stiffness; second, the blood flow changes due to the pressure wave. Accordingly, different methods can be used to measure PWV. One method disclosed herein measures the rate of change of a vessel diameter (vessel-diameter-change speed), which is the basis for a dual M-mode method. Another method disclosed herein measures changes in blood-flow velocity (blood-flow-change speed), which is the basis for a dual-PW method. Yet another method disclosed herein is a combination of measuring the vessel-diameter-change speed and the blood-flow-change speed, which is the basis for a combination M-mode and PW method. Further details of these methods and other features are described below.

Example Ultrasound System

FIG. 1 illustrates an example environment for an ultrasound system 100 having an ultrasound scanner, in accordance with one or more implementations. Generally, the ultrasound system 100 includes an ultrasound machine 102, which generates data based on high-frequency sound waves reflecting off body structures. The ultrasound machine 102 includes various components, some of which include a scanner 104, one or more processors 106, a display device 108, and a memory 110.

A user 112 (e.g., nurse, ultrasound technician, clinician, operator, sonographer) directs the scanner 104 toward a patient 114 (e.g., a human or animal) to non-invasively scan internal bodily structures (anatomies, organs, tissues, etc.) of the patient 114 for testing, diagnostic, or therapeutic reasons. In some implementations, the scanner 104 includes an ultrasound transducer array and electronics communicatively coupled to the ultrasound transducer array to transmit ultrasound signals to the patient's anatomy and receive ultrasound signals reflected from the patient's anatomy (e.g., echoes) as part of an ultrasound examination. In some implementations, the scanner 104 is an ultrasound scanner, which can also be referred to as an ultrasound probe or transducer.

The display device 108 is coupled to the processor 106, which processes the reflected ultrasound signals to generate ultrasound data. The display device 108 is configured to generate and display an ultrasound image (e.g., ultrasound image 116) of the anatomy based on the ultrasound data generated by the processor 106 from the reflected ultrasound signals detected by the scanner 104. In some aspects, the ultrasound data includes the ultrasound image 116 or data representing the ultrasound image 116.

Figure 2:
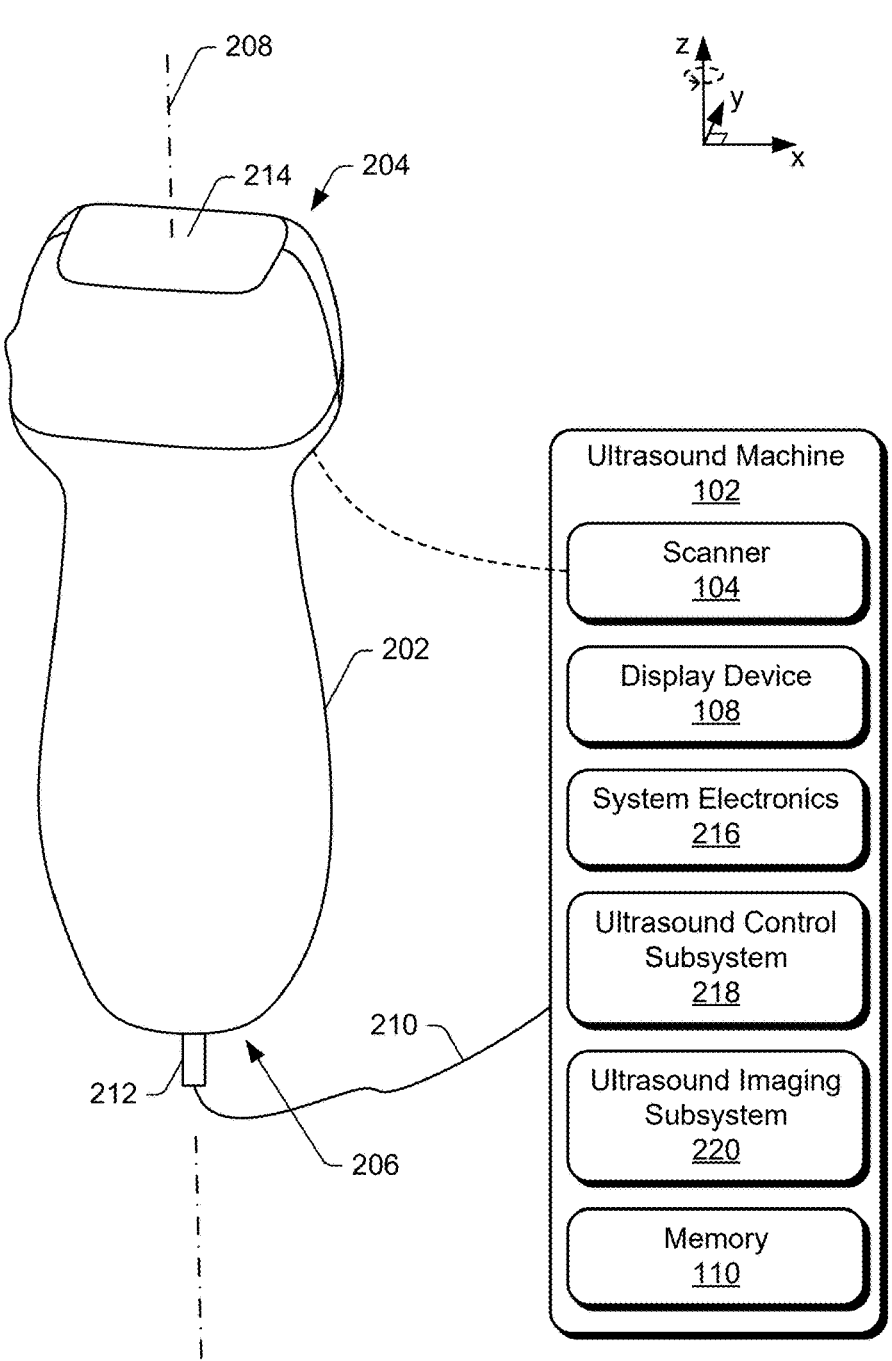
FIG. 2 illustrates an example implementation of the ultrasound system from FIG. 1.

FIG. 2 illustrates an example implementation 200 of the ultrasound system 100 from FIG. 1. The scanner 104 (e.g., ultrasound scanner) includes an enclosure 202 extending between a distal end portion 204 and a proximal end portion 206. The enclosure 202 includes a central axis 208 (e.g., longitudinal axis) that intersects the distal end portion 204 and the proximal end portion 206. The central axis 208 corresponds to an axial direction of the scanner 104. In an example, the scanner 104 is electrically coupled to an ultrasound imaging system (e.g., the ultrasound machine 102) via a cable 210 that is attached to the proximal end portion 206 of the scanner 104 by a strain-relief element 212. In some implementations, the scanner 104 is wirelessly coupled to the ultrasound imaging system and communicates with the ultrasound imaging system via one or more wireless transmitters, receivers, or transceivers over a wireless connection or network (Bluetooth™, Wi-Fi™, etc.).

A transducer assembly 214 having one or more transducer elements is electrically coupled to system electronics 216 in the ultrasound machine 102. In operation, the transducer assembly 214 transmits ultrasound energy from the one or more transducer elements toward a subject and receives ultrasound echoes from the subject. The ultrasound echoes are converted into electrical signals by the transducer element(s) and electrically transmitted to the system electronics 216 in the ultrasound machine 102 for processing and generation of one or more ultrasound images.

Capturing ultrasound data from a subject using a transducer assembly (e.g., the transducer assembly 214) generally includes generating ultrasound signals, transmitting ultrasound signals into the subject, and receiving ultrasound signals reflected by the subject. A wide range of frequencies of ultrasound can be used to capture ultrasound data, such as, for example, low-frequency ultrasound (e.g., less than 15 megahertz (MHz)) and/or high-frequency ultrasound (e.g., greater than or equal to 15 MHz). A particular frequency range to use can readily be determined based on various factors, including, for example, depth of imaging, desired resolution, and so forth.

In some implementations, the system electronics 216 include one or more processors (e.g., the processor(s) 106 from FIG. 1), integrated circuits, application-specific integrated circuits (ASICs), Field Programmable Gate Arrays (FPGAs), Graphics Processing Units (GPUs) and power sources to support functioning of the ultrasound machine 102. In some implementations, the ultrasound machine 102 also includes an ultrasound control subsystem 218 having one or more processors. At least one processor, FPGA, ASIC, or GPU causes electrical signals to be transmitted to the transducer(s) of the scanner 104 to emit sound waves and also receives electrical pulses from the scanner 104 that were created from the returning echoes. One or more processors, FPGAs, ASICs, or GPUs process the raw data associated with the received electrical pulses and form an image that is sent to an ultrasound imaging subsystem 220, which causes the image (e.g., the image 116 in FIG. 1) to be displayed via the display device 108. Thus, the display device 108 displays ultrasound images from the ultrasound data processed by the processor(s) of the ultrasound control subsystem 218.

In some implementations, the ultrasound machine 102 also includes one or more user input devices (a keyboard, a cursor control device, a microphone, a camera, etc.) that input data and enable taking measurements from the display device 108 of the ultrasound machine 102. The ultrasound machine 102 can also include a disk storage device (e.g., computer-readable storage media such as read-only memory (ROM), a Flash memory, a dynamic random-access memory (DRAM), a NOR memory, a static random-access memory (SRAM), a NAND memory, and so on) for storing the acquired ultrasound data. In aspects, the disk storage device includes the memory 110, which is local to the ultrasound machine 102. Alternatively, the memory 110 used for storing the acquisition data can be remote, such as on a remote server communicatively connected to the ultrasound machine 102. In addition, the ultrasound machine 102 can include a printer that prints the image from the displayed data. To avoid obscuring the techniques described herein, such user input devices, disk storage device, and printer are not shown in FIG. 2.

Figure 3:
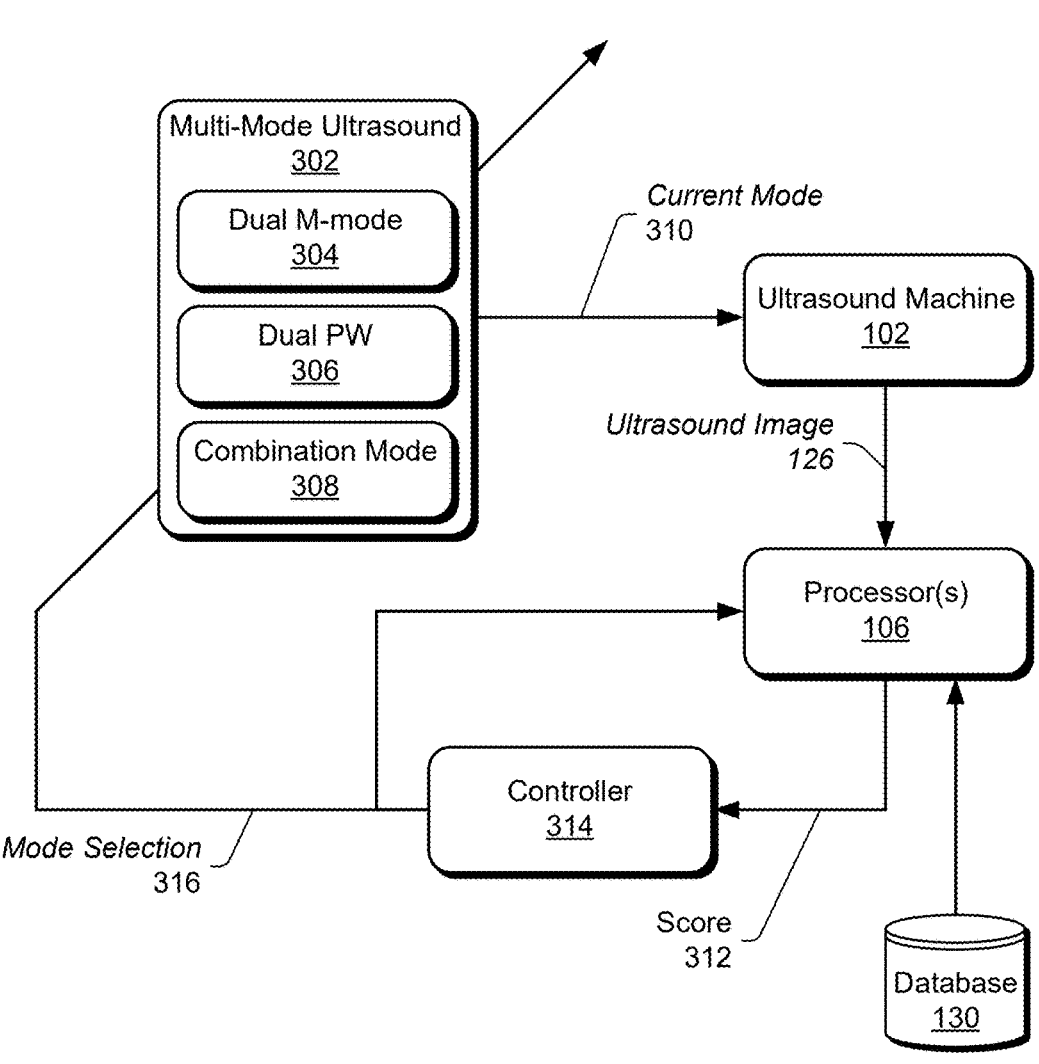
FIG. 3 illustrates an example implementation of a multimode ultrasound in accordance with one or more implementations.

FIG. 3 illustrates an example implementation 300 of a multi-mode ultrasound 302 in accordance with one or more implementations. The ultrasound modes illustrated and described with respect to FIG. 3 are described as examples and the implementations disclosed herein are not intended to be limited to these examples. The techniques disclosed herein can be implemented with other ultrasound modes that are not described herein. Accordingly, the list of example ultrasound modes is not an exhaustive list.

The multi-mode ultrasound 302 includes various combinations of modes utilized by the ultrasound control subsystem 218 to process raw data associated with received signals from the transducer(s). In implementations, the ultrasound control subsystem 218 can use multiple ultrasound modes to process the raw ultrasound data to measure physiological properties. Such a multi-mode operation can include a dual implementation of a particular mode, including M-mode, pulsed wave (PW) Doppler (also referred to herein as "PW"), etc. For example, the multi-mode ultrasound 302 can include a dual M-mode 304, a dual PW 306, or a combination mode 308. The combination mode is a combination of two or more different modes, including M-mode+PW, a combination of B-mode+M-mode+PW Doppler, a combination of B-mode+M-mode+color Doppler+PW Doppler, etc. In implementations, the user can selectively choose which combination of modes the ultrasound system uses. If, for example, a high frame rate is desired, then the user may select the dual M-mode 304, the dual PW 306, or a combination mode including M-mode and PW Doppler used simultaneously.

In some aspects, the ultrasound machine 102 uses a first mode (e.g., current mode 310), which can be selected by the user or initialized by a setting. Using the current setting 310, the ultrasound machine 102 generates the ultrasound image 126. The ultrasound image 126 is sent to the processor(s) 106, which uses the ultrasound image 126 to determine one or more factors, including image quality, protocol step, neural-network inference, etc. In one example, the processor(s) 106 can receive an inference from a neural network using the ultrasound image 126 as an input. In addition, the processor(s) 106 can determine a confidence factor associated with the one or more factors, such as a weight assigned to each factor. The processor(s) 106 can use, as input for determining the one or more factors and the confidence factor, various data from the database 130, including protocol data, user data, patient history, previous measurements of BP and/or PWV, etc.

The processor(s) 106 can use the one or more factors and the confidence factor to determine a score 312 for the ultrasound image 126. The score 312 is provided to a controller 314. The controller 314 can use the score 312 to select a mode of the multi-mode ultrasound 302 for use in generating subsequent ultrasound images. The controller 314 can generate a mode selection 316 for the multi-mode ultrasound 302. The mode selection 316 can select the same mode as the current mode 310. In aspects, the mode selection 316 can select a mode that is different from the current mode 310 to enable the ultrasound machine 102 to generate an improved ultrasound image having, for example, a higher image quality for obtaining more-accurate measurements.

Dual M-mode

Figure 4:
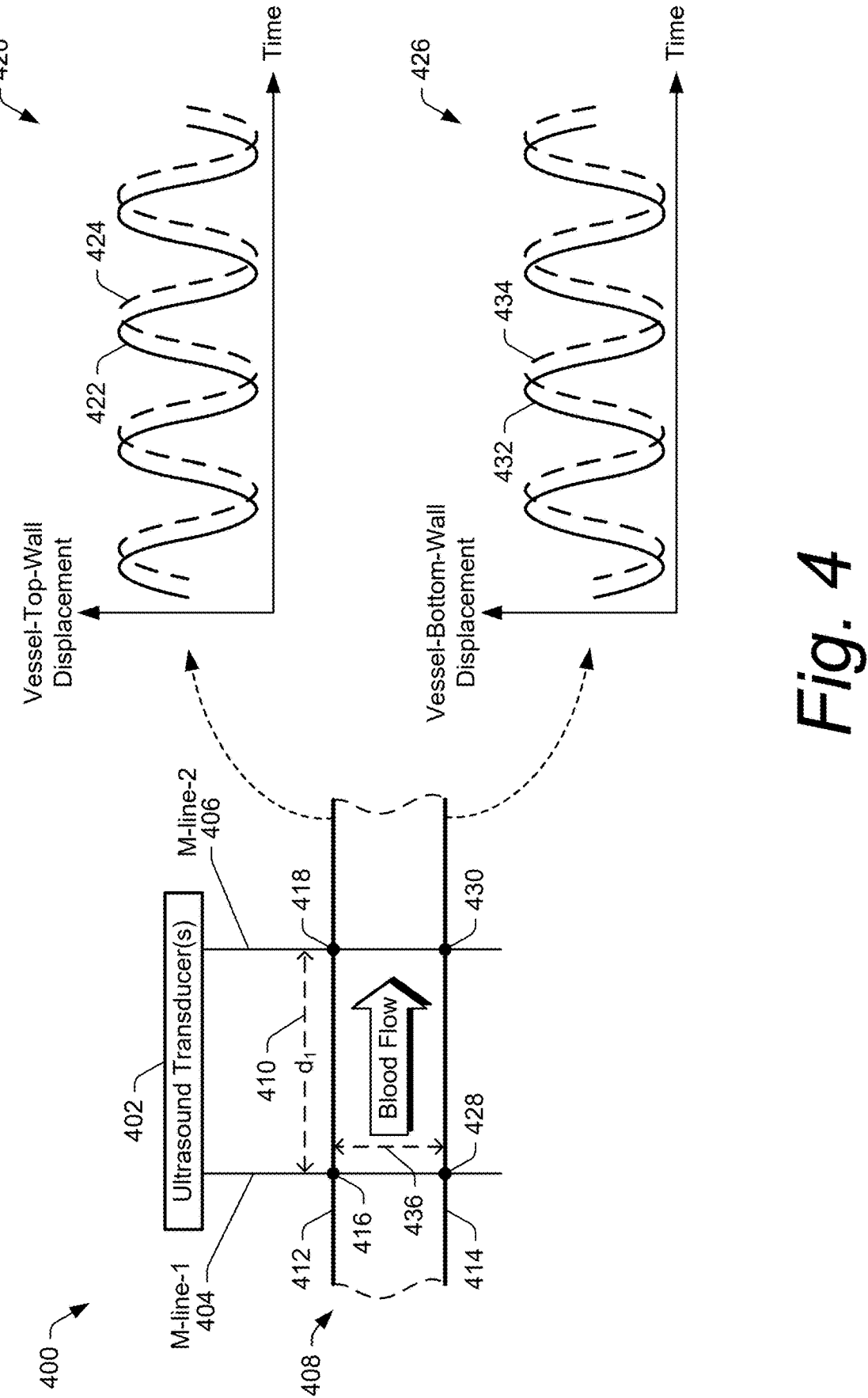
FIG. 4 illustrates an example implementation of measuring PWV using dual M-mode ultrasound.

FIG. 4 illustrates an example implementation of measuring PWV using a dual M-mode ultrasound (e.g., dual M-mode 304 in FIG. 3). In this example, to measure PWV, an ultrasound scanner applies two M-lines on the same blood vessel (e.g., an artery) with a known distance between the two M-lines. For example, setup 400 shows one or more ultrasound scanner(s) 402 (e.g., scanner 104) applying two M-mode lines (e.g., M-line-1 404 and M-line-2 406) at two locations on a vessel 408 that are separated by a distance $d_1$ 410. The distance $d_1$ 410 is known (e.g., predefined), such as a defined distance between the two M-lines. The two M-lines can be applied by the same scanner or two separate scanners. When applied by a single scanner, the distance $d_1$ 410 is small (5 mm, 2 mm, between 1 and 0.001 mm, etc.), such that the two M-lines are applied without physically moving the scanner. The distance $d_1$ 410 can be determined based on the transducer elements used to generate the two M-lines. For example, the transducer elements used to generate the M-lines are separated by a fixed distance, which is equal to the distance $d_1$ 410. The distance $d_1$ 410 can be greater when applied by separate scanners; however, a greater distance $d_1$ 410 may be less accurately defined and can therefore reduce the accuracy of the PWV calculations. When applied by separate scanners, each scanner can include a position-measuring sensor, such as an internal measurement unit (IMU) that measures positional data of the scanner. The positional data can include an acceleration, an angular rate, and/or an orientation of the scanner. The distance $d_1$ 410 can be estimated based on the positional data generated by the IMU of each scanner and the firing of the ultrasound transducer array of each scanner.

Due to the pulse wave passing through the vessel 408 and based on a stiffness (or flexibility) of the vessel, the vessel wall moves, resulting in changes to the diameter of the vessel. The rate of movement of the vessel wall, or the rate of change of the vessel diameter, is related to the PWV. Using the dual M-mode 304 method, the PWV can be quantified in various ways, including measurement of (i) a vessel's top-wall-displacement speed, (ii) a vessel's bottom-wall-displacement speed, or (iii) a rate of change of the vessel diameter (e.g., distance between the top wall and the bottom wall of the vessel).

As described herein, the top wall and bottom wall are defined relative to the ultrasound scanner 402. For example, the "top" wall (e.g., top wall 412) is the vessel wall nearest to the scanner 402 such that the top wall is the first surface of the vessel encountered by the ultrasound signals transmitted by the scanner 402. In contrast, the "bottom" wall (e.g., bottom wall 414) is the vessel's opposing wall from the top wall and is farther from the scanner 402 than the top wall.

In a first example, only the top-wall-displacement speed is measured along the vessel. The ultrasound scanner 402 applies the M-line-1 404 on the vessel 408 at an upstream location and the M-line-2 406 at a downstream location relative to the direction of blood flow in the vessel 408. The M-line-1 404 passes through the vessel 408 at a first location 416 on the top wall 412 and the M-line-2 406 passes through the vessel 408 at a second location 418 on the top wall 412.

Plot 420 represents the displacement of the top wall 412 of the vessel 408 over time, where the displacement is caused by pulse waves pushing blood through the vessel 408. The solid curve (e.g., curve 422) represents the displacement over time of the top wall 412 of the vessel 408 at the first location 416, as detected via the M-line-1 404. The dashed curve (curve 424) represents the displacement over time of the top wall 412 of the vessel 408 at the second location 418, as detected via the M-line-2 406. As the blood flows from left to right in the vessel 408 of the setup 400, the vessel wall from M-line-1 404 changes first due to the pulse wave, and the vessel wall from M-line-2 406 changes at a later time. The time difference between the changes at the two locations (e.g., the first location 416 from M-line-1 404 and the second location 418 from M-line-2 406) is a pulse propagation time (PPT), which can be calculated from a time shift between the two curves in the plot 420. The time shift between the two curves can be determined using any suitable technique, including a cross-correlation method, a phase-shift calculation (e.g., time difference divided by wave period), transformation formula, etc. The cross-correlation method can determine the integral of the product of the two curves at multiple positions along the x-axis to find a maximum (or minimum) value of the product of the two curves. The determined maximum (or minimum) value indicates the two curves match. The time delay between the two curves can therefore be determined by the argument of the maximum (or minimum) of the cross-correlation. The PPT can be expressed as:

$$PPT = \Delta t + t_P \qquad \text{Eq. (1)}$$

where $\Delta t$ is the time shift from the two curves in the plot 420, and $t_p$ is the time difference between the M-line-1 404 and the M-line-2 406. Here, it is assumed that lines are fired alternately at positions of the M-line-1 404 and the M-line-2 406. In an example, the M-line-1 404 is fired first, then the M-line-2 406 is subsequently fired, followed by another firing of M-line-1 404, and then again M-line-2 406. Such alternating firing of the M-lines can avoid mixing signals. Therefore, the PWV can be calculated as:

$$PWV = \frac{d}{PPT \times \sin\theta} \qquad \text{Eq. (2)}$$

where $\theta$ is an angle between the blood vessel and the M-line and d is the distance (e.g., distance $d_1$ 410) between the M-lines. Because the distance d is predefined, its value is known for the calculations. If the vessel is parallel to the scanner, PWV can be reduced to:

$$PWV = \frac{d}{PPT} \qquad \text{Eq. (3)}$$

For a typical linear transducer, the transducer size is around 40 millimeters (mm). To measure the PWV of, for example, 10 m/s, the PPT is around 4 milliseconds (ms). To satisfy the Nyquist sampling criteria, the frame rate of each M-line needs to be about 1000 frames per second (fps). In aspects, the M-line-1 404 and M-line-2 406 can be acquired alternately to avoid mixing signals.

To increase the frame rate, an encoding and decoding mechanism can be used to fire both M-lines and acquire the data within a time interval (including a zero time interval, e.g., simultaneously). One example method is to use a bipolar Hadamard encoding and decoding processes for M-line-1 and M-line-2. For M-line-1, the signals generated with a $Tx_1$ waveform can be described as $S(\text{M-line-1})=Rx_1$. For M-line-2, the signals generated with a $Tx_2$ waveform can be described as $S(\text{M-line-2})=Rx_2$. If $Tx_1$ an $Tx_2$ are mixed together with both having positive polarity, the generated signals with this encoded waveform can be expressed as $S(\text{M-line-1+M-line-2})$, for example:

$$S(M{-}line{-}1 + M{-}line{-}2) = Rx_1 + Rx_2 \qquad \text{Eq. (4)}$$

For simplicity, the first mixed transmit and receive event is referred to as Ping1. The received radio-frequency (RF) data of Ping1 $RF_{Ping1}$ can be expressed as:

$$RF_{Ping1} = RF_1 + RF_2 \qquad \text{Eq. (5)}$$

where $RF_1$ is the RF data of M-line-1 from transmit $Tx_1$, and $RF_2$ is the RF data of M-line-2 from transmit $Tx_2$. For a second mixed transmit and receive event, Ping2, $Tx_1$ still has positive polarity while $Tx_2$ has negative polarity. Combining these two, the transmit of Ping2 is $Tx_1+(-Tx_2)$, and $Tx_1-Tx_2$ is used instead to represent the Ping2 transmit. Accordingly, the signals with this encoded waveform can be expressed as $S(\text{M-line-1-M-line-2})$:

$$S(M{-}line{-}1 - M{-}line{-}2) = Rx_1 - Rx_2 \qquad \text{Eq. (6)}$$

The received RF data of Ping2 $RF_{Ping2}$ can be expressed as:

$$RF_{Ping2} = RF_1 - RF_2 \qquad \text{Eq. (7)}$$

Based on Eqs. (5) and (7), the RF data of M-line-1, which is $RF_1$, and the RF data of M-line-2, which is $RF_2$, can be recovered by using the following expressions:

$$RF_1 = (RF_{Ping1} + RF_{Ping2})/2 \qquad \text{Eq. (8)}$$

$$RF_2 = (RF_{Ping1} - RF_{Ping2})/2 \qquad \text{Eq. (9)}$$

where the decode Hadamard matrix has the same form of the encode matrix, which is:

$$\begin{bmatrix} 1 & 1 \\ 1 & -1 \end{bmatrix}$$

In this case, after using the encoding and decoding process, the M-line-1 and M-line-2 can be fired and acquired at the same time, which increases the frame rate by a factor of 2 and increases the range and accuracy of the PWV measurement. Note that other encoding methods can also be used, including unipolar Hadamard, Fourier, Wavelet, etc. The Hadamard matrix described above is exemplary and not meant to be limiting.

Although the above description uses the displacement of the top wall of the vessel from two M-lines to calculate PWV, the PWV can also be calculated using the displacement of the bottom wall of the vessel, as shown in plot 426. For example, the calculation process is the same as using the top wall displacement of the vessel except the M-lines measure displacement at a third location 428 and a fourth location 430, respectively, on the bottom wall 414 of the vessel 408. Then, curves 432 and 434, shown in the plot 426, represent displacement over time of the bottom wall 414 at the third and fourth locations 428 and 430, respectively.

In addition, using the same process, a change of distance between the top and bottom walls (e.g., vessel diameter 436) can be measured and used to calculate the PWV. For example, M-line-1 404 can be used to detect the change to the diameter 436 between the first location 416 on the top wall 412 and the third location 428 on the bottom wall 414. The M-line-2 406 can be used to detect the change to the diameter 436 between the second location 418 on the top wall 412 and the fourth location 430 on the bottom wall 414. Then, the time difference (e.g., pulse propagation time) between when the changes occur along the M-line-1 404 and when corresponding changes occur along the M-line-2 406 is used to calculate the PWV, using Equations (1)-(9).

Dual PW (With or Without Encoding)

Figure 5:
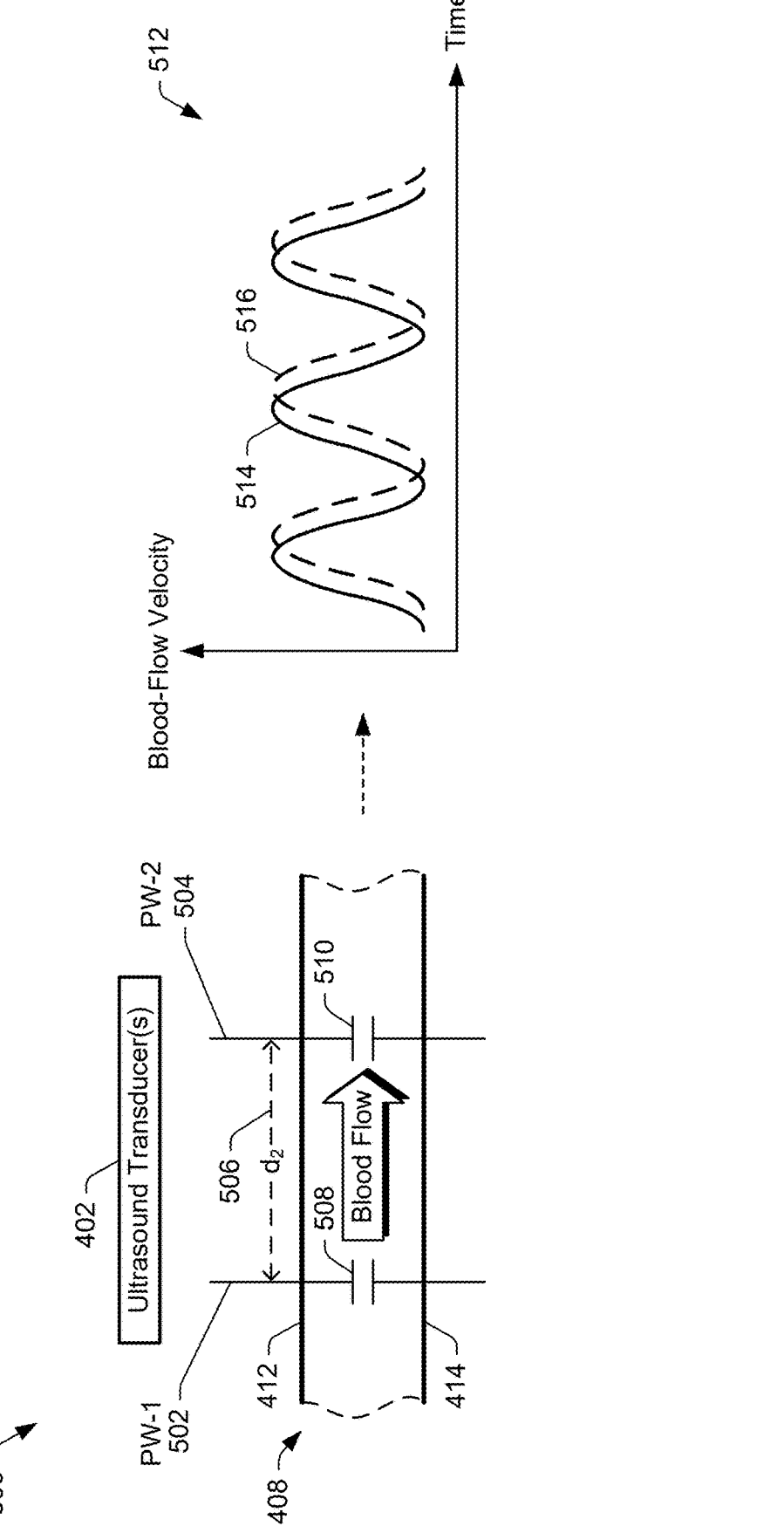
FIG. 5 illustrates an example implementation of measuring PWV using dual—pulsed-wave (PW) Doppler.

FIG. 5 illustrates an example implementation of measuring PWV using dual-PW Doppler (e.g., dual PW 306 in FIG. 3). As mentioned, dual PW is another method usable to measure the rate of change of blood flow (e.g., blood-flow-change speed or blood-flow-velocity change). As shown in FIG. 5, the principle and calculation processes are similar to the dual M-mode method described above, but the dual-PW method is different in that the blood flow is measured at upstream and downstream positions of a blood vessel. Then, by quantifying the blood-flow-change delays in these two positions, PWV can be calculated.

For example, setup 500 includes the ultrasound scanner(s) 402 applying two PW lines (e.g., PW-1 502 and PW-2 504) with gates (e.g., sample volumes) positioned inside the same vessel (e.g., vessel 408) at locations 506 and 508 that are separated by a distance $d_2$ 510. The two PW lines can be applied by the same scanner or two separate scanners. The distance $d_2$ 510 between the PW lines is known. When applied by a single scanner, the distance $d_2$ 510 is small (e.g., 5 mm, 3 mm, 1 mm, between 1 and 0.001 mm), such that the two PW lines are applied without physically moving the scanner 402. The distance $d_2$ 510 can be greater when applied by separate scanners; however, a greater distance $d_2$ 510 can be less accurately defined and can therefore reduce the accuracy of the PWV calculations. The PW-1 502 line corresponds to a first location 506 in the vessel 408 and the PW2 504 line corresponds to a second location 508 in the vessel 408.

Plot 512 represents blood-flow velocity measured over time. The solid curve (e.g., curve 514) is blood-flow velocity measured from the PW-1 line (e.g., PW-1 502). The dashed curve (e.g., curve 516) is blood-flow velocity measured from the PW-2 line (e.g., PW-2 504). As blood flows from left to right in the vessel 408 of the setup 500, the blood-flow velocity at PW-1 502 changes first due to the pulse wave, and the blood-flow velocity at PW-2 504 changes later. The time difference between the blood-flow-velocity change at the two locations (e.g., the first location 506 and the second location 508) represents the pulse propagation time (PPT), which can be calculated from the time shift between the two curves in plot 512 (e.g., curve 514 and curve 516). The time shift can be calculated based on a cross-correlation method applied to the two curves in plot 512. Such calculations are based on equations similar to those described above for the dual M-mode example, including Eqs. (1)-(9), where the distance $d_2$ 510 is used as the distance d in the calculations. In addition, a similar encoding and decoding method can also be applied.

The vessel-wall movement (described with respect to FIG. 4) and the blood-flow-velocity change (described with respect to FIG. 5) are the two results caused by a pulse wave. Therefore, if both the vessel-wall movement and the blood-flow-velocity change are measured, a more accurate measurement of the PWV can be achieved. One way to measure both the vessel-wall movement and the blood-flow-velocity change is to use dual PW only, as described herein with respect to FIG. 6. Another method is to combine the dual M-mode 304 and dual PW 306 methods, which is described with respect to FIG. 7 in more detail.

Figure 6:
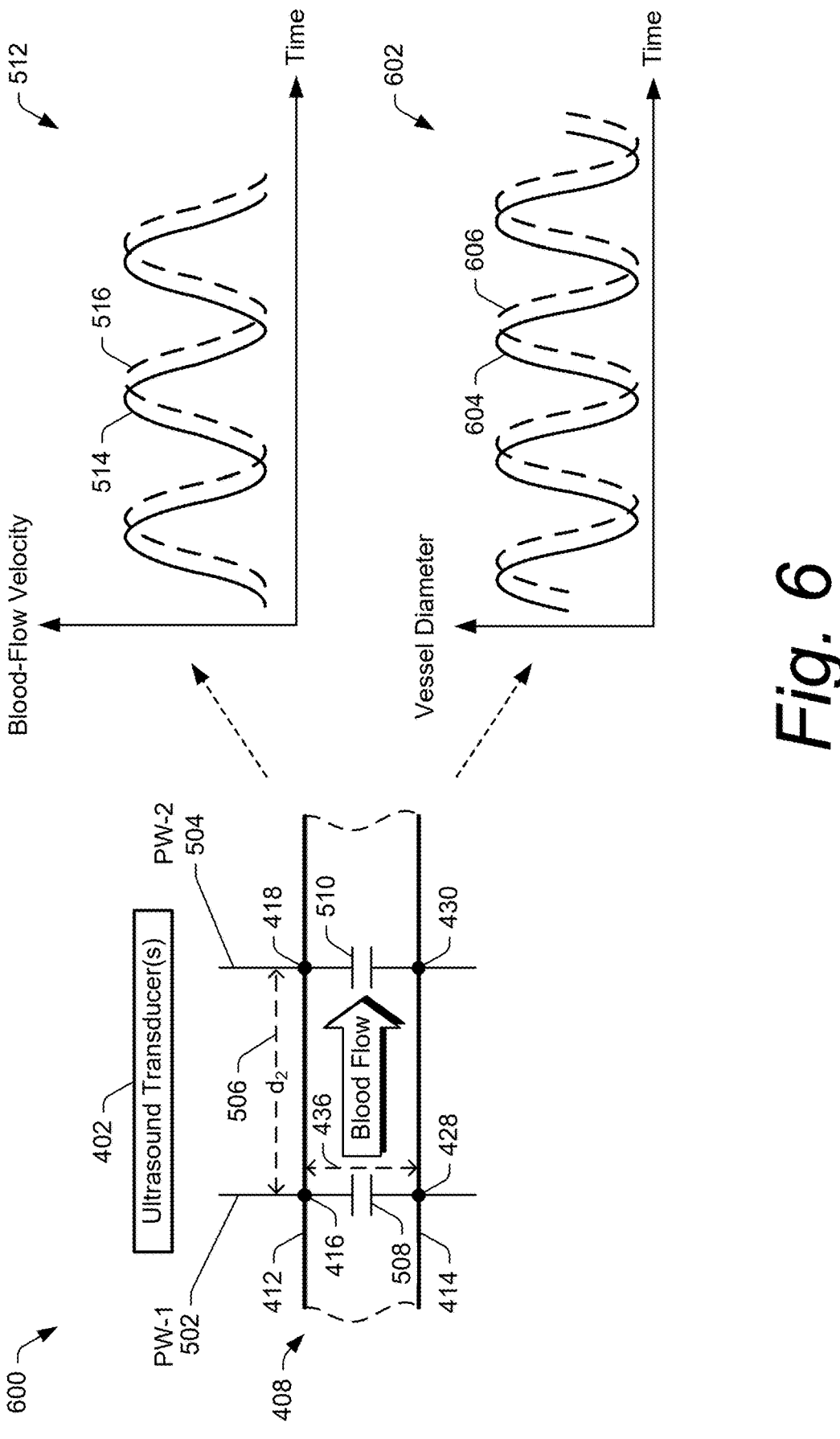
FIG. 6 illustrates an example implementation of using dual-PW Doppler to measure both PWV and vessel-wall movement.

FIG. 6 illustrates an example implementation of using a dual-PW method (e.g., dual PW 306 in FIG. 3) to measure both blood-flow-velocity changes and vessel-wall movement. Although the PW waveform usually is long in order to have a narrow bandwidth and better flow measurement sensitivity, the PW waveform is still a pulse. Accordingly, prior to performing the PW-blood-flow process, a typical beamforming method can be implemented to form a line image (similar to M-mode) and thus calculate the vessel-wall displacement and eventually vessel diameter. The spatial resolution may be low in the dual PW method, but such spatial resolution is sufficient to measure the vessel diameter and thus measure the PWV.

As shown in FIG. 6, setup 600 is the same as the setup 500 in FIG. 5. However, in addition to measuring the blood-flow-velocity changes over time (as shown in plot 512) using the dual PW method described above, displacement of the blood vessel's top wall 412 and bottom wall 414 can also be extracted (similar to plots 420 and 426 in FIG. 4). Then, based on locations associated with the top and bottom walls (e.g., the first location 416, the second location 418, the third location 428, and the fourth location 430), the vessel diameter 436 can be calculated, as shown in plot 602. The solid line (e.g., curve 604) represents the vessel diameter 436 as calculated using the measurements extracted from the first location 416 and the third location 428 using PW-1 502. The dashed line (e.g., curve 606) represents the vessel diameter 436 as calculated using the measurements extracted from the second location 418 and the fourth location 430 using PW-2 504.

Note that although the illustrated example in FIG. 6 shows vessel-diameter measurements in plot 602, it is enough to measure PWV just based on the vessel's top-wall displacement or bottom-wall displacement, as shown and described with respect to FIG. 4 (e.g., plots 420 and 426).

Combination Mode

Figure 7:
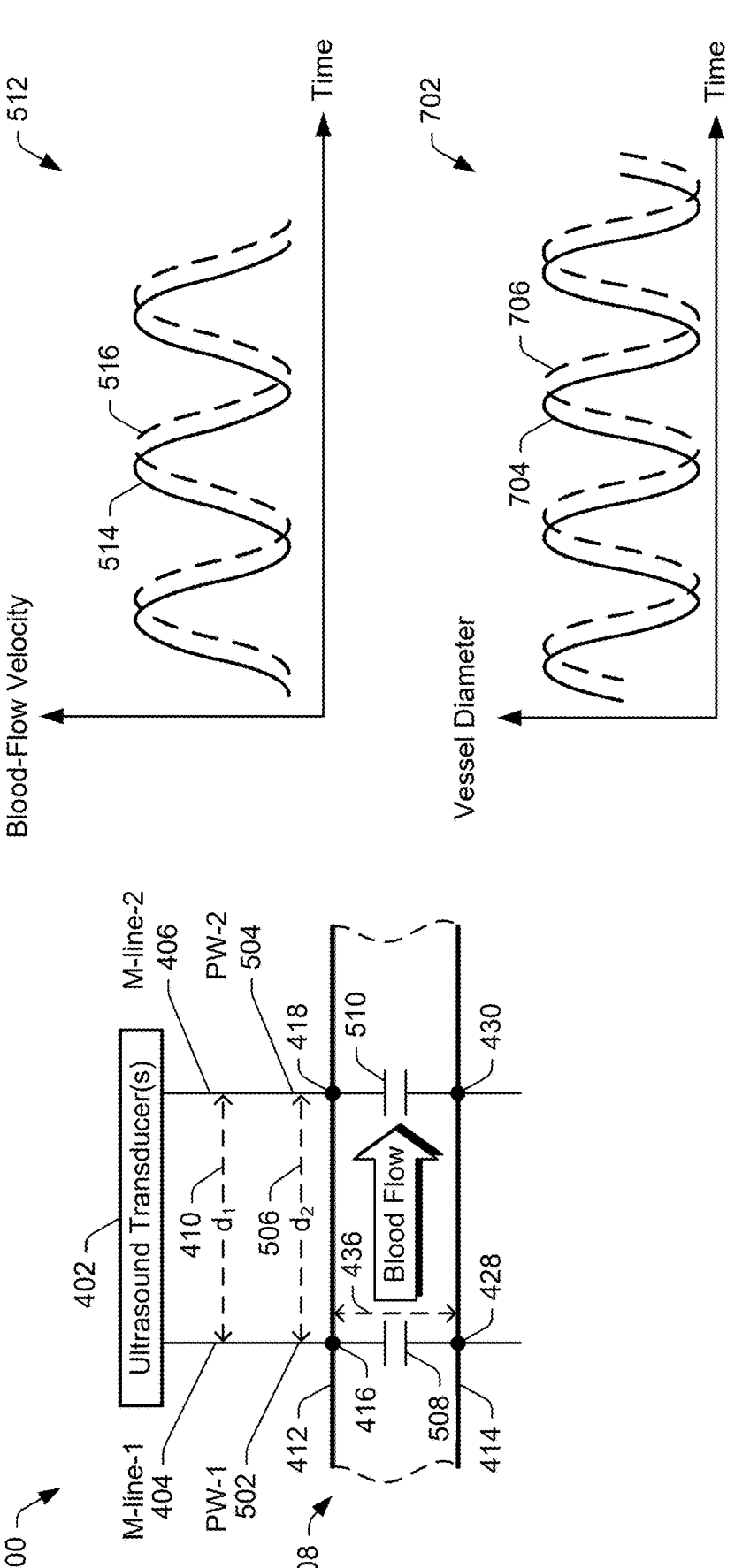
FIG. 7 illustrates an example implementation of using a combination mode to measure PWV.

FIG. 7 illustrates an example implementation of using a combination mode to measure PWV. In particular, the illustrated example uses a combination of the dual M-mode 304 and the dual PW 306 to measure PWV. A setup 700 for measurement includes two M-lines (e.g., M-line-1 404, M-line-2 406) used to measure the same vessel and two PW lines (e.g., PW-1 502, PW-2 504) with respective gates inside the vessel and used to measure the same vessel. An M-line and a PW line can be aligned (same vertical line) or have different positions. For simplicity, the example described in FIG. 7 shows M-lines placed at the same positions as the PW lines. However, the techniques described herein can also be implemented with the M-lines being offset (e.g., unaligned) from the PW lines. In the example illustration, the distance $d_1$ 410 between the M-mode lines is the same as the distance $d_2$ 510 between the PW lines. In practice, the distances $d_1$ and $d_2$ are not required to be the same, as long as the distances $d_1$ and $d_2$ are accurately determined when used to calculate the PWV, as indicated in Equation (3).

Using dual M-mode together with dual PW can enhance the spatial resolution. In this case, if dual M-mode lines and dual-PW lines are fired alternately (continually following and succeeded by each other, one after the other, e.g., interleaved), then the frame rate becomes half with respect to the dual M-mode or the dual PW, which can limit the maximum measurable PWV to be half. However, because M-mode has better spatial resolution than PW, the measurement accuracy from wall displacement and diameter of the blood vessel is expected to be better than the result from dual PW.

The change in blood-flow velocity over time is illustrated in plot 512 and is measured using the techniques described herein with respect to FIG. 5. For example, the solid curve (e.g., curve 514) is blood-flow velocity measured from PW-1 502 at the first location 506 and the dashed curve (e.g., curve 516) is blood-flow velocity measured from PW-2 504 at the second location 508. As disclosed above, the time difference between the blood-flow-velocity changes at these two locations represents the pulse propagation time (PPT), which can be calculated from the time shift between the two curves in plot 512 (e.g., curve 514 and curve 516). The time shift can be calculated based on a cross-correlation method applied to the two curves in plot 512.

The change in vessel diameter over time is illustrated in plot 702. In plot 702, the solid line (e.g., curve 704) represents changes to the vessel diameter 436 over time as determined using the M-line-1 404 to measure vessel-wall displacement of the top and bottom walls of the vessel 408, as measured at the first location 416 on the top wall 412 and the third location 428 on the bottom wall 414. The dashed line (e.g., curve 706) represents the changes to the vessel diameter 436 over time as determined using the M-line-2 406 to measure vessel-wall displacement of the vessel 408, as measured at the second location 418 on the top wall 412 and the fourth location 430 on the bottom wall 414. In some implementations, however, it is sufficient to measure PWV just based on the displacement of the top wall 412 of the vessel 408 or the displacement of the bottom wall 414 of the vessel 408, as described with respect to FIG. 4.

To increase the frame rate, similar encoding and decoding methods can be used on dual M-mode and dual PW. Instead of encoding two modes, four modes are encoded (two M-mode lines and two PW lines). Therefore, a Hadamard bipolar method of order four can be used. In this case, the frame rate can be increased by a factor of four. Other similar encoding methods can also be used, including unipolar Hadamard, Fourier, Wavelet, etc.

To calculate PWV, the ultrasound machine 102 measures vessel-wall movement and blood-flow change. Therefore, any ultrasound modes that can be used to measure vessel-wall movement and blood-flow change are applicable. For example, the ultrasound machine 102 can use (i) a high frame rate B-mode image, or anatomic M-mode, to measure the vessel-wall movement and (ii) high frame rate color flow imaging to measure the change in blood-flow velocity. Such a procedure is similar to the dual M-mode 304 or the dual PW 306, which are used to measure one property (vessel-wall movement or blood flow) at an upstream location and the same property (vessel-wall movement or blood flow) at a downstream location of the same vessel. Then based on a correlation method, the PPT is calculated and used to calculate PWV with the known distance between the two locations.

Blood Pressure Measurement

After successfully obtaining a PWV measurement, the blood pressure (BP) can be estimated based on the Moens-Koreweg (MK) and Hughes equations:

$$PWV = \sqrt{\frac{Eh_0}{2\rho R_0}} \qquad \text{Eq. (10)}$$

$$E = E_0 \exp(\tau BP) \qquad \text{Eq. (11)}$$

where E is the elastic modulus at blood pressure BP, $h_0$ is the thickness of the vessel (e.g., artery), and $R_0$ is the radius of the vessel. In addition, $\rho$ is the blood density, $E_0$ is the elastic modulus at zero blood pressure, and $\tau$ is a material coefficient of the vessel. As shown in Equations (10) and (11), as the blood pressure BP increases, the PWV increases as well. The relationship between BP and PWV can be expressed as follows:

$$BP = \frac{1}{\tau} \ln\left(\frac{4(\rho R_0 PWV)^2}{h_0 E_0}\right) \qquad \text{Eq. (12)}$$

Using Equation (12), the blood pressure BP can be determined based on the PWV. One technique to measure BP based on PWV is to use an empirical method, which is first to measure a series of patients with different PWVs and BPs, and then based on Eq. (12), perform a regression to determine the coefficients between PWV and BP. In that case, a universal empirical formula is established and can be used to predict BP based on PWV in a future patient. Another technique to measure BP based on PWV is to establish a formula based on one patient's data and use that formula for future measurements of other patients. In some implementations, machine learning (ML) can be used to determine BP based on PWV. An ML model can ignore the above-described equations. For example, an ML model is established based on a collection of data, such as measurements from a series of patients with different PWVs and BPs, and then the ML model is used to predict the BP in a new patent based on a measured PWV of that new patient.

By using the techniques disclosed herein (dual M-mode, dual PW, dual M-mode+dual PW, etc.), other important physiological properties can also be measured with increased accuracy. For example, M-mode and PW can be used at the same blood-vessel position to measure blood volume in real time with high accuracy. Blood volume per second (BVS) can be calculated as:

$$BVS = \frac{\pi d^2 V}{4} \qquad \text{Eq. (13)}$$

where d is the diameter of the vessel and V is the blood-flow velocity. Compared to conventional methods for measuring BVS, which are generally based on a B-mode image to measure vessel diameter, the disclosed techniques can provide significantly higher temporal resolution (e.g., frame rate) for BVS measurement. A fast frame rate is critical for various applications, including cardiac function monitoring. For example, the M-line and PW gate can both be placed on a valve, such as a mitral valve, a tricuspid valve, a pulmonary valve, or an aortic valve. Then, a corresponding ejection fraction can be measured with a high frame rate and high accuracy.

Another application of using M-mode and PW to monitor the same location on a vessel is to quantify the phase delay of a pulse wave along the vessel wall and the blood. Although the pulse-wave source is the same (e.g., from the heart), the propagation along the vessel wall and the blood stream depend on other physiological properties, such as vessel-wall stiffness and blood viscosity. Therefore, by monitoring the delays of the pulse wave along the vessel wall and inside the blood stream, the vessel-wall stiffness and the blood viscosity can each be calculated.

Dual M-mode and dual PW can also be used to measure the blood volume at upstream and downstream locations in the same vessel at the same time. Not only can PWV be measured, but these techniques can also be used to calculate conservation of the blood volume by comparing the blood-volume-measurement results from the two locations. Then, based on the comparison of the blood-volume-measurement results, the ultrasound system can determine potential leakage or blockage of the blood vessel.

Other implementations can include using M-mode and PW on the same position. For example, the relative phase shift between vessel-wall-displacement speed and blood-velocity changes can indicate one or more physiological properties of the heart and of the vessel between the measurement point and the heart. M-mode and PW can be used on the same position (valve, artery, etc.) to measure the vessel-diameter-change speed and the blood-flow velocity at the same time, which can enable blood flux to be quantitatively monitored in real time.

By using M-mode and PW on two positions, such as the example described with respect to FIG. 7, a difference in blood flux at the two positions can be measured. The difference in blood flux at the two positions can be used to determine blood perfusion and blood-perfusion indexes.

Accordingly, different ultrasound-imaging modes can be combined to maximize the capability of the modes used. For example, for PWV measurement, a higher pulse-repetition frequency (PRF) of M-mode and/or PW provides enhanced measurement results.

Example Methods

FIGS. 8 and 9 depict methods 800 and 900, respectively, for using ultrasound to measure physiological properties. The methods 800 and 900 are shown as a set of blocks that specify operations performed but are not necessarily limited to the order or combinations shown for performing the operations by the respective blocks. Further, any of one or more of the operations can be repeated, combined, reorganized, or linked to provide a wide array of additional and/or alternate methods. In portions of the following discussion, reference can be made to the example system 100 of FIG. 1 or to entities or processes as detailed in FIGS. 2-7, reference to which is made for example only. The techniques are not limited to performance by one entity or multiple entities operating on one device.

FIG. 8 depicts a method 800 for using ultrasound to measure physiological properties. The method 800 can be performed by the ultrasound system 100. At 802, a multi-mode ultrasound is applied to acquire ultrasound data at two locations of a same vessel that are separated by a known distance. For example, multiple ultrasound modes (e.g., dual M-mode 304, dual PW 306, combination mode 308) can be used by the ultrasound control subsystem 218 to process the raw ultrasound data associated with received signals from the scanner 402, where the received signals are received from two locations separated by a known distance.

At 804, one or more characteristics of the vessel is measured at each of the two locations. For example, the ultrasound machine 102 can measure one or more characteristics of the vessel 408 at each of the two locations, including vessel-wall-displacement speed, blood-flow-change speed, etc.

At 806, a phase delay of a pulse wave along the vessel between the two locations is quantified based on a correlation between the one or more characteristics of the vessel at the two locations. For example, the one or more characteristics (vessel-wall-displacement speed, blood-flow-change speed, etc.) are used to determine the pulse propagation time (PPT) of the pulse wave propagating through the vessel 408.

At 808, a physiological property associated with the vessel is calculated based on the known distance and the phase delay. For example, the distance d and the PPT can be used to calculate the PWV. In aspects, the PWV can be calculated by the ultrasound system 100 using at least some of the Eqs. (2)-(9) disclosed above.

In some aspects, at 810, one or more additional physiological properties associated with the vessel are determined based on the calculated physiological property. For example, the calculated physiological property (e.g., PWV) can be used to calculate an additional physiological property, such as BP, associated with the vessel 408.

FIG. 9 depicts a method 900 for measuring physiological properties using ultrasound. The method 900 can be implemented by the ultrasound system 100. At 902, first ultrasound data corresponding to a first location on a vessel is acquired over a duration of time. In one example, the M-line-1 404 is applied to an upstream location (e.g., the first location 416, the third location 428). In another example, the PW-1 502 line is applied to the first location 506.

At 904, second ultrasound data corresponding to a second location on the vessel is acquired over the duration of time, where the second location is separated from the first location by a known distance. In one example, the M-line-2 406 is applied to a downstream location (e.g., the second location 418, the fourth location 430), where the downstream location is separated from the upstream location by the distance $d_1$ 410. In another example, the PW-2 504 gate is applied to the second location 508, where the second location is separated from the first location 506 by the distance $d_2$ 510.

At 906, at least one of a rate of vessel-wall displacement of the vessel or blood-flow-velocity changes in the vessel is measured over the duration of time based on the first ultrasound data and the second ultrasound data. For example, vessel-wall-displacement speed can be measured using the M-mode lines. Alternatively, the blood-flow-velocity changes can be measured using the PW lines.

At 908, a pulse-propagation time of a pulse wave along the vessel is calculated based on a correlation of the at least one of the vessel-wall displacement or the blood-flow-velocity changes between the first and second locations. For example, the pulse-propagation time of a pulse wave propagating through the vessel 408 can be calculated based on a phase delay of the vessel-wall-displacement speed between the first location 416 and the second location 418, or between the third location 428 and the fourth location 430. In another example, the pulse-propagation time of a pulse wave propagating through the vessel 408 can be calculated based on a phase delay of the blood-flow-velocity changes between the first location 506 and the second location 508.

At 910, a pulse-wave velocity of blood in the vessel is determined based on the pulse-propagation time and the known distance. For example, the ultrasound system 100 can use Equations (1)-(9) to determine the PWV.

In some aspects, at 912, one or more physiological properties associated with the vessel is determined based on the pulse-wave velocity. For example, blood pressure can be determined based on the pulse-wave velocity. Other physiological properties can be determined, including vessel-wall stiffness, blood viscosity, blood volume, blood perfusion, blood-perfusion indexes, and so on.

Example Machine-Learned Models

Figure 10:
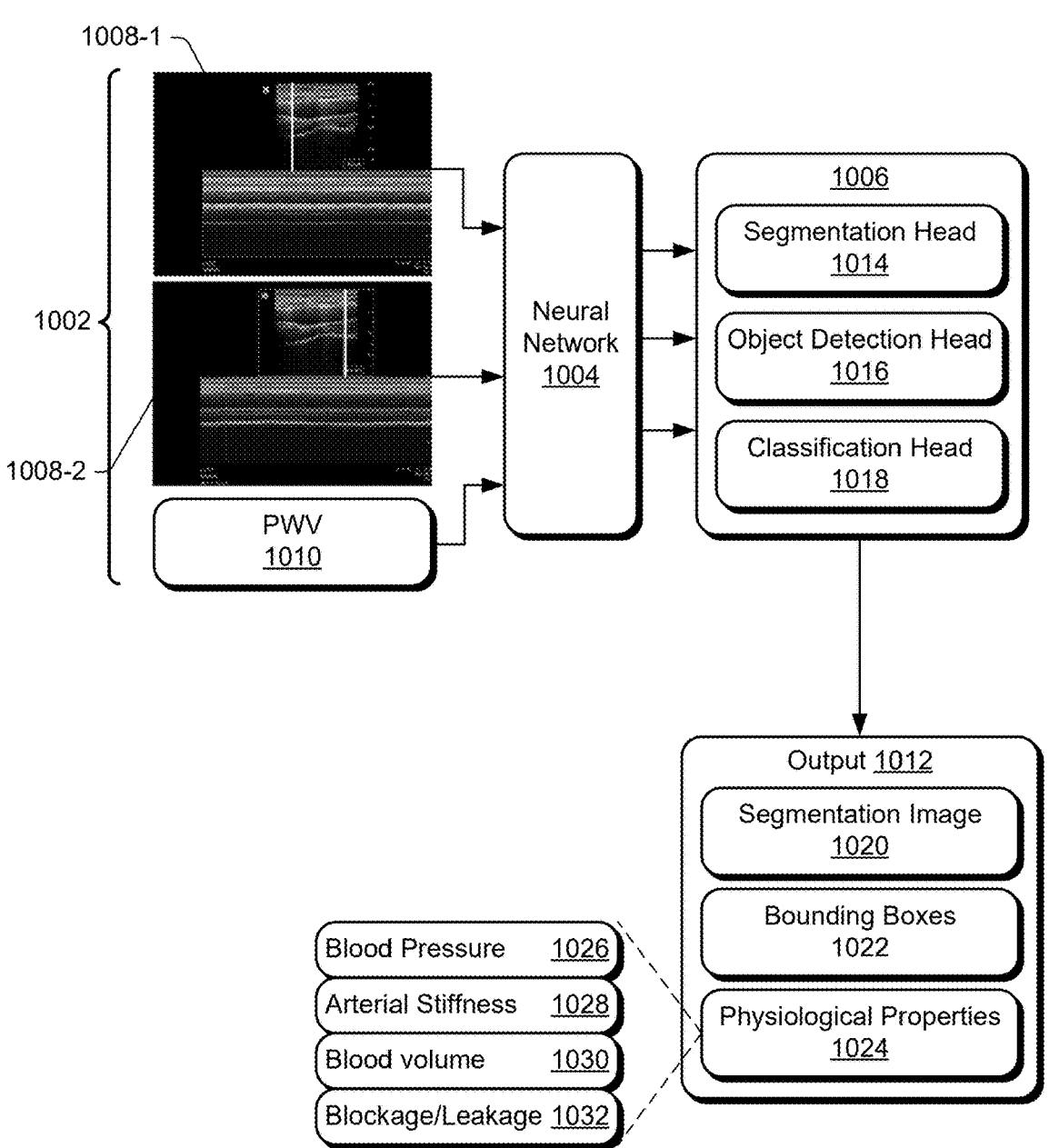
FIG. 10 represents an example machine-learning (ML) model for processing an input from an ultrasound device.

FIG. 10 represents an example ML model for processing an input from an ultrasound device (e.g., the ultrasound machine 102). In aspects, an ML model 1000 can include inputs 1002, a neural network 1004, and a generation module 1006. The inputs 1002 can, by way of example, include ultrasound data, which can be used to generate ultrasound images 1008 (e.g., first M-mode image 1008-1, second M-mode image 1008-2) and a PWV 1010 corresponding to the ultrasound data and/or the ultrasound images 1008. Additionally or alternately, the ultrasound images 1008 and the PWV 1010 can be used as the inputs 1002 for the ML model 1000 to provide an output 1012.

According to some implementations, the generation module 1006 can comprise a segmentation head 1014, an object detection head 1016, a classification head 1018, or more or fewer components. The segmentation head 1014 can, in some examples, highlight structures of interest in the inputs 1002, such as by generating segmentations of the structures and/or segmentation images 1020. According to some embodiments, the object detection head 1016 can generate bounding boxes 1022 of structures of interest in the inputs 1002. The classification head 1018 can, for example, determine physiological properties 1024 from the inputs 1002. The physiological properties are properties associated with the vessel, and can include blood pressure 1026, arterial stiffness 1028, blood volume 1030, blockage/leakage 1032, etc. Using such an ML model can increase the accuracy of the determined physiological properties in comparison to the approximations calculated using the deterministic approach (e.g., Equations (10)-(13)).

The inputs 1002 can, in some implementations, be input as data, such as a matrix or other, multi-dimensional mathematical object, the ultrasound data generated by the ultrasound scanner 104, and so on. In aspects, the neural network 1004 can include a feature-extraction component, such as a convolutional neural network (CNN). The neural network

1004 can, in some examples, comprise several different neural network architectures known to a person of ordinary skill in the art and can comprise any combination of like or different architectures. According to some embodiments, the neural network 1004 can comprise a single architecture type. These example neural network architectures and combinations are listed as examples only and are not meant to limit the scope of the neural network 1004. It should be noted that the neural network 1004, for example, can comprise a network other than a learning network, as can be construed by the term "neural network." Rather, in aspects the neural network 1004 can comprise an algorithm derived from a machine-learning training, as is explained below.

Many of the aspects described herein can be implemented using an ML model. For the purposes of this disclosure, an ML model is any model that accepts an input, analyzes and/or processes the input based on an algorithm derived via machine-learning training, and provides an output. An ML model can be conceptualized as a mathematical function of the following form:

$$f(\hat{s}, \theta) = \hat{y} \qquad \text{Equation (14)}$$

In Equation (14), the operator f can represent the processing of the ML model based on an input and providing an output. The term $\hat{s}$ can represent a model input, such as ultrasound data, optical data, or both or other data. The ML model can analyze/process the input $\hat{s}$ using parameters $\theta$ to generate an output $\hat{y}$ (e.g., object identification, object segmentation, object classification). Both the input $\hat{s}$ and the output $\hat{y}$ can be scalar values, matrices, vectors, or mathematical representations of phenomena such as categories, classifications, image characteristics, the images themselves (e.g., the ultrasound image 116), text, labels, or the like. The parameters $\theta$ can be any suitable mathematical operations, including but not limited to applications of weights and biases, filter coefficients, summations or other aggregations of data inputs, distribution parameters such as mean and variance in a Gaussian distribution, linear algebra-based operators, or other parameters, including combinations of different parameters, suitable to map data to a desired output.

Figure 11:
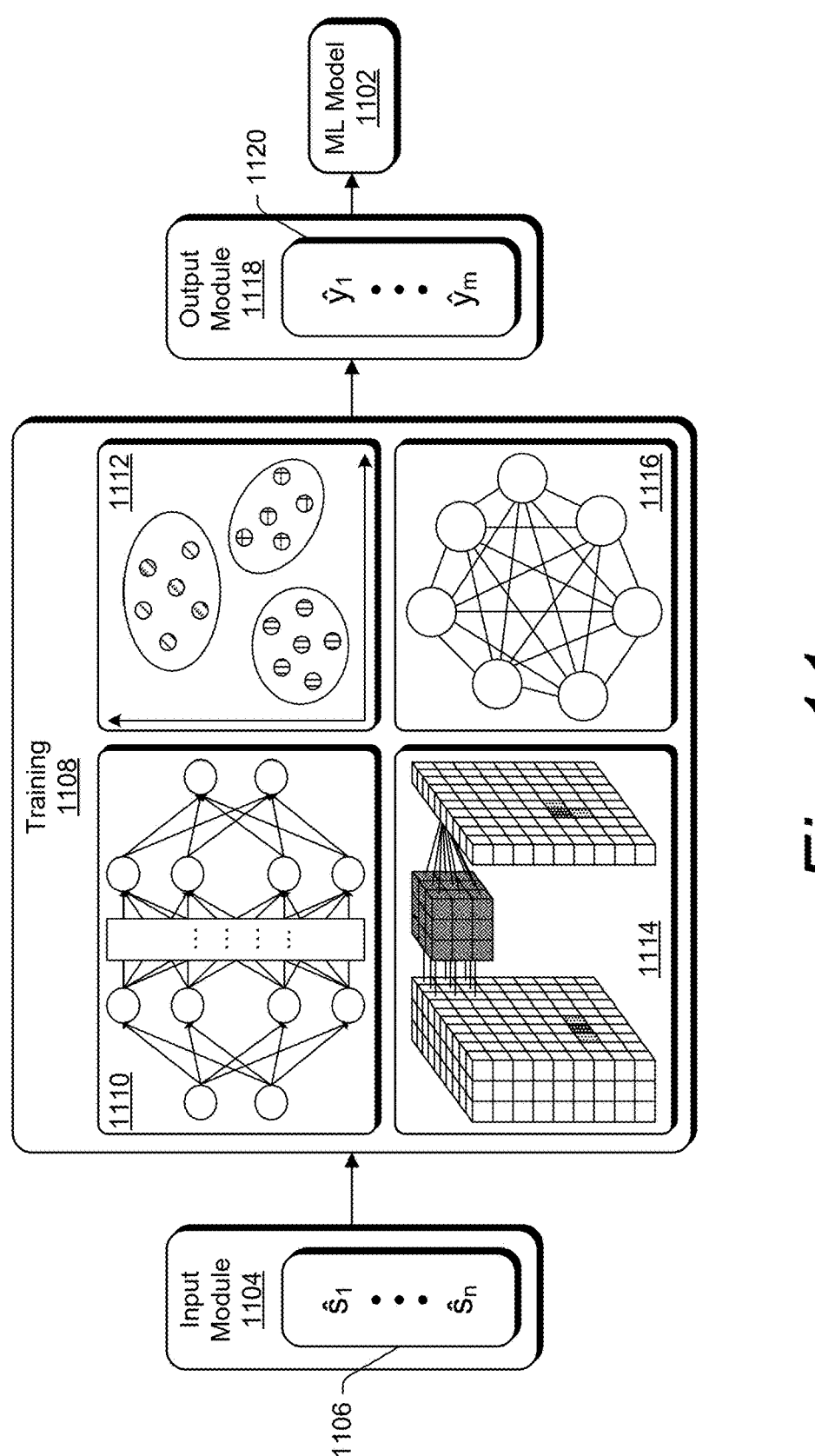
FIG. 11 represents an example machine-learning architecture used to train an ML model.

FIG. 11 represents an example machine-learning architecture 1100 used to train an ML model 1102 (e.g., ML model 1000). An input module 1104 can accept an input $\hat{s}$ 1106, which can be an array with members $\hat{s}_1$ through $\hat{s}_n$. The members of the array can be multidimensional, or the array itself can instead be a matrix or other mathematical object holding multiple points or vectors of data values. The input $\hat{s}$ 1106 can be fed into a training module 1108, which can process the input $\hat{s}$ 1106 based on the machine-learning architecture 1100. For example, if the machine-learning architecture 1100 uses a multilayer perceptron (MLP) model 1110, the training module 1108 applies weights and biases to the input $\hat{s}$ 1106 through one or more layers of perceptrons, each perceptron performing a fit using its own weights and biases according to its given functional form. The MLP weights and biases can be adjusted such that they are optimized against a least mean square, logcosh, or other optimization function (e.g., loss function) known in the art. Although the MLP model 1110 is described here as an example, any suitable machine-learning technique can be employed, some examples of which include but are not limited to k-means clustering 1112, convolutional neural networks (CNN) 1114, a Boltzmann machine 1116, a Gaussian mixture model (GMM), and a long short-term memory (LSTM). The training module 1108 can provide an input to an output module 1118. The output module 1118 can analyze the input from the training module 1108 and provide an output in the form of ŷ 1120, which can be an array with members $\hat{y}_1$ through $\hat{y}_m$, or another single- or multiple-dimensional object. The output ŷ 1120 can represent a known correlation with the input ŝ 1106, such as, for example, object identification, segmentation, and/or classification.

In some examples, the input ŝ 1106 can be a training input labeled with known output correlation values, and these known values can be used to optimize the output ŷ 1120 in training against the optimization/loss function. In other examples, the machine-learning architecture 1100 can categorize the output ŷ 1120 values without being given known correlation values to the inputs ŝ 1106. In some examples, the machine-learning architecture 1100 can be a combination of machine-learning architectures. By way of example, a first network can use the input ŝ 1106 and provide the output ŷ 1120 as an input $\hat{s}_{ML}$ to a second machine-learned architecture, with the second machine-learned architecture providing a final output $\hat{y}_f$. In another example, one or more machine-learning architectures can be implemented at various points throughout the training module 1108.

In some machine-learned models, all layers of the model can be fully connected. For example, all perceptrons in the MLP model 1110 act on every member of ŝ. For the MLP model 1110 with a 100×100 pixel image as an input, each perceptron provides weights/biases for 10,000 inputs. With a large, densely layered model, this can result in slower processing and/or issues with vanishing and/or exploding gradients. The CNN 1114, which can, in some constructions, not be a fully connected model, can process the same image using 5×5 tiled regions, requiring only 25 perceptrons with shared weights, giving much greater efficiency than the fully connected MLP model 1110. Additionally or alternately, the training module 1108 can employ sections of architecture that are fully connected and sections that are not. By way of example, the input ŝ 1106 can be a matrix representing data from both an ultrasound image and an optical image and the training module 1108 can use the CNN 1114 to identify features from the input ŝ 1106. The features can then be used as auxiliary inputs for the MLP model 1110, which can subsequently give an output to the output module 1118. The CNN 1114 portion of this example is not fully connected, but the MLP 1110 portion is fully connected, where every perceptron in a first layer takes every input from the CNN 1114 and all perceptrons are causally connected to the eventual input for the output module 1118. Other architecture types and combinations can be employed by a person of ordinary skill in the art, and the foregoing example is not meant to be limiting, but illustrative.

Figure 12:
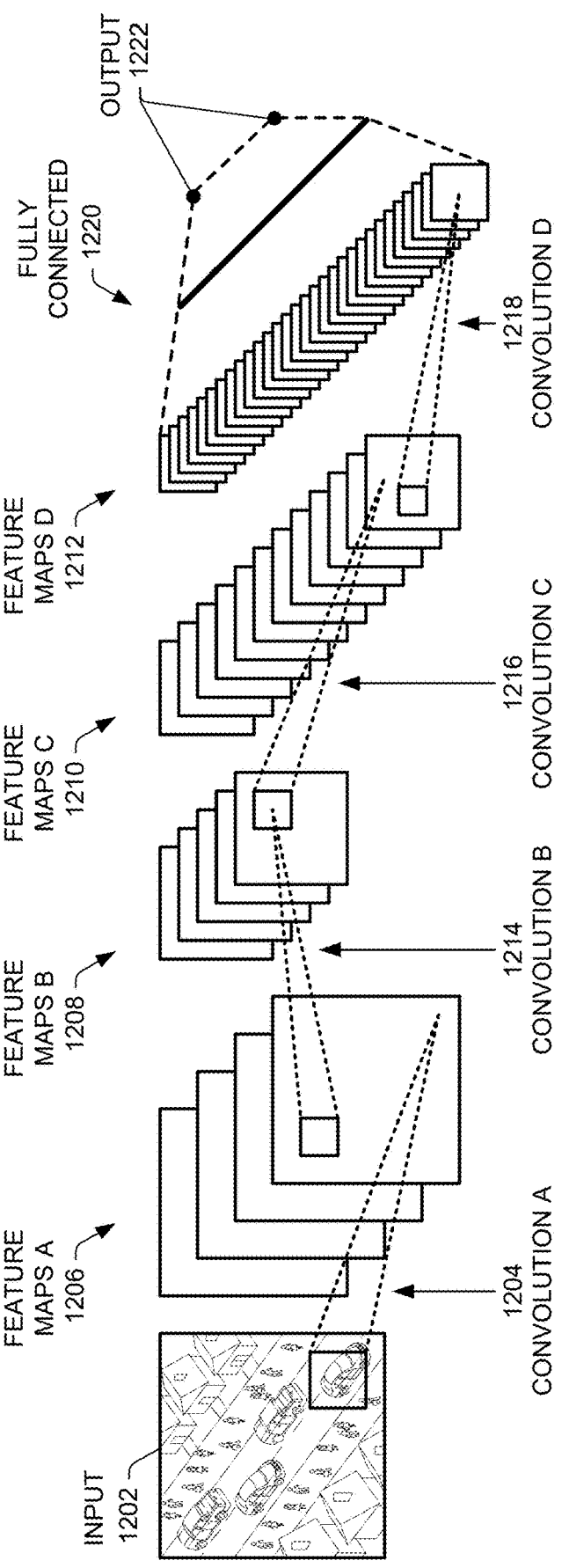
FIG. 12 represents an example model using a convolutional neural network (CNN) to process an input image, which can include representations of objects that can be identified via object recognition.

FIG. 12 represents an example model 1200 using a CNN to process an input image 1202, which can include representations of objects that can be identified via object recognition, such as people or cars (or an anatomy, such as the vessel 408). Convolution A 1204 can be performed, for example, to create a first set of feature maps (e.g., feature maps A 1206). A feature map can be a mapping of aspects of the input image 1202 given by a filter element of the CNN. This process can be repeated using, by way of example, feature maps A 1206 to generate further feature maps B 1208, feature maps C 1210, and feature maps D 1212 using convolution B 1214, convolution C 1216, and convolution D 1218, respectively. In this example, feature maps D 1212 can become an input for fully connected network layers 1220. In this way, the example model 1200 can be trained to recognize certain elements of the image, such as people, cars, or a particular patient anatomy, and provide an output 1222 (a prediction, an inference, etc.) that, for example, can identify the recognized elements. Additionally or alternately, each feature map, such as feature maps C 1210, can contain multiple feature maps. It is possible for some feature maps to be a set of multiple feature maps and others to be a single feature map. By way of example, feature maps A 1206 can be multiple feature maps, each using a variation of the CNN architecture of the example model 1200, and feature maps B 1208 can be a single feature map.

Although the example of FIG. 12 shows a CNN as a part of a fully connected network, other architectures are possible, and this example should not be seen as limiting. There can be more or fewer layers in the CNN. The CNN component for the model can be placed in a different order, or the model can contain additional components or models. In some examples, there are no fully connected components, such as in a fully convolutional network. Additional aspects of the CNN, such as pooling, down-sampling, up-sampling, or other aspects known to a person of ordinary skill in the art, can also be employed.

Figure 13:
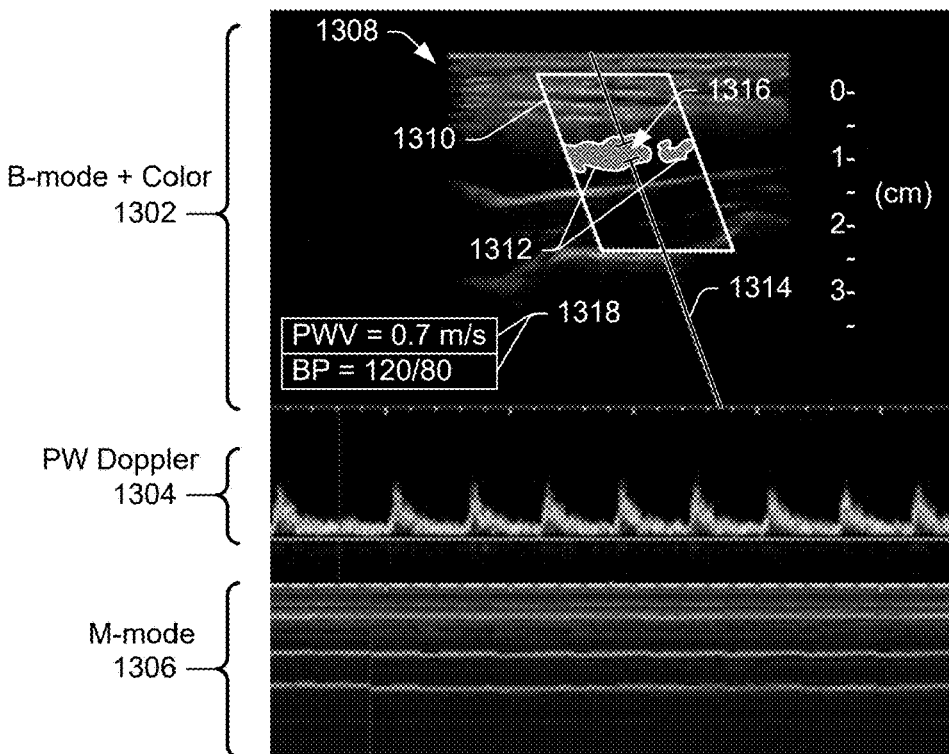
FIG. 13 illustrates an example user interface displayed via a display device coupled to the ultrasound system from FIG. 1, in accordance with one or more implementations.

FIG. 13 illustrates an example user interface 1300 displayed via a display device (e.g., the display device 108) coupled to the ultrasound system 100 from FIG. 1, in accordance with one or more implementations. In aspects, the user interface 1300 can be used to provide results of multiple different ultrasound imaging modes, including those described with respect to FIGS. 3-12. In the illustrated example, the user interface 1300 includes a first portion 1302, a second portion 1304, and a third portion 1306. The user interface 1300 can include additional (or fewer) portions for presenting ultrasound information.

In an example, the first portion 1302 of the user interface 1300 can be used to present an ultrasound image 1308 generated by the ultrasound system 100 using B-mode plus color Doppler. The color Doppler can be superimposed or overlaid over the B-mode image. For example, a section 1310 of the B-mode image (e.g., the ultrasound image 1308) can be selected for color Doppler analysis. In FIG. 13, dotted areas 1312 represent colored areas displayed over the B-mode image. The dotted areas 1312 are colored with a color that represents fluid flow in a direction. A different color can be used to represent fluid flow in an opposing direction (e.g., red for a first flow direction and blue for a second, opposite flow direction).

The second portion 1304 of the user interface 1300 can be used to present results associated with PW Doppler measurements corresponding to a PW line 1314 having a gate 1316 selected or placed in the ultrasound image 1308 in the first portion 1302 of the user interface 1300. The third portion 1306 of the user interface 1300 can be used to present results associated with M-mode ultrasound corresponding to one or more M-lines selected or placed in the ultrasound image 1308 in the first portion 1302 of the user interface 1300. In the illustrated example, the M-line is collocated with the PW line 1314. However, the M-line can be placed at a different location than the PW line 1314. Although only one PW line 1314 is shown, multiple PW lines 1314 and/or M-lines can be used, as described with respect to FIGS. 5-7, to determine a physiological property such as PWV.

Accordingly, the user interface 1300 can be used to provide information corresponding to a plurality of ultrasound modes simultaneously. In addition to providing the ultrasound mode information (e.g., the ultrasound image 1308, the PW results, the M-mode results, etc.), the user interface 1300 can also provide an indication of one or more physiological properties 1318, as disclosed above. The physiological properties, as determined from the ultrasound data associated with the ultrasound image 1308, can include PWV, blood pressure, arterial stiffness, blood volume, blockage/leakage percentage, etc.

CONCLUSION

Ultrasound methods and systems for measuring physiological properties are disclosed. These ultrasound techniques provide highly accurate measurements of physiological properties of a subject by reducing errors associated with distance estimations between the measurement location and the heart. Additionally, these ultrasound techniques provide a way to measure physiological properties, such as pulse-wave velocity and blood pressure, using only ultrasound and without relying on the assistance of ECG data.

What is claimed is:

1. An ultrasound system comprising:
an ultrasound scanner configured to generate ultrasound data based on reflections of ultrasound signals transmitted by the ultrasound scanner at an anatomy, the ultrasound scanner configured to acquire the ultrasound data at two locations of a same vessel that are separated by a distance, the ultrasound data acquired at the two locations within a time interval;
one or more processors; and
one or more computer-readable storage media having instructions stored thereon that, responsive to execution by the one or more processors, cause the one or more processors to:
determine a vessel-diameter-change speed over time and a blood-flow-velocity change over time of the vessel at each of the two locations using the ultrasound data;
determine, based on a correlation between the vessel-diameter-change speed and the blood-flow-velocity change of the vessel at the two locations, a phase delay of a pulse wave propagating through the vessel between the two locations; and
determine a physiological property associated with the vessel based on the vessel-diameter-change speed, the blood-flow-velocity change, the phase delay, and the distance.

2. The ultrasound system of claim 1, wherein the physiological property is a pulse-wave velocity of the pulse wave.

3. The ultrasound system of claim 2, wherein the instructions further cause the one or more processors to determine, based on the pulse-wave velocity, blood viscosity and vessel-wall stiffness associated with the vessel.

4. The ultrasound system of claim 2, wherein the instructions further cause the one or more processors to predict, using a machine-learned model stored on the one or more computer-readable storage media, blood pressure based on the physiological property associated with the vessel.

5. The ultrasound system of claim 1, wherein the instructions further cause the one or more processors to determine, based on the physiological property, one or more additional physiological properties associated with the vessel.

6. The ultrasound system of claim 5, wherein the one or more additional physiological properties include at least one of blood pressure, blood volume per second, vessel-wall stiffness, or blood viscosity.

7. The ultrasound system of claim 1, wherein the vessel-diameter-change speed and the blood-flow-velocity change are measured without using electrocardiogram (ECG) data.

8. The ultrasound system of claim 1, wherein the ultrasound scanner is configured to acquire the ultrasound data at the two locations using dual M-mode or dual-PW Doppler.

9. The ultrasound system of claim 1, further comprising determining the distance that separates the two locations based on transducer elements used to generate the ultrasound signals at each of the two locations.

10. The ultrasound system of claim 1, wherein the ultrasound scanner is configured to acquire the ultrasound data at the two locations using two or more modes including two or more of an M-mode, a PW Doppler, a color Doppler, and a B-mode.

11. The ultrasound system of claim 1, wherein the ultrasound scanner is a single scanner configured to transmit the ultrasound signals at the two locations simultaneously.

12. The ultrasound system of claim 1, wherein the ultrasound scanner is a single scanner and transmission of the ultrasound signals is interleaved between the two locations.

13. A method comprising:
acquiring ultrasound data at two locations of a same vessel that are separated by a distance, the ultrasound data acquired at the two locations within a time interval;
determining a vessel-diameter-change speed over time and a blood-flow-velocity change over time of the vessel at each of the two locations using the ultrasound data;
determining, based on a correlation between the vessel-diameter-change speed and the blood-flow-velocity change of the vessel at the two locations, a phase delay of a pulse wave propagating through the vessel between the two locations; and
determining a physiological property associated with the vessel based on the vessel-diameter-change speed, the blood-flow-velocity change, the phase delay, and the distance.

14. The method of claim 13, wherein determining the physiological property includes calculating a pulse-wave velocity of the pulse wave propagating through the vessel.

15. The method of claim 13, further comprising determining, based on the physiological property, one or more additional physiological properties associated with the vessel.

16. The method of claim 15, wherein determining the one or more additional physiological properties includes determining at least one of blood pressure, blood volume per second, vessel-wall stiffness, or blood viscosity.

17. The method of claim 13, wherein acquiring the ultrasound data at the two locations includes using dual M-mode ultrasound by applying a first M-line at a first location of the two locations and a second M-line at a second location of the two locations.

18. The method of claim 13, wherein acquiring the ultrasound data at the two locations includes using dual-PW Doppler by applying a first PW line at a first location of the two locations and a second PW line at a second location of the two locations.

19. The method of claim 13, wherein acquiring the ultrasound data at the two locations includes using two or more of an M-mode, a PW Doppler, a color Doppler, and a B-mode.

20. The method of claim 13, wherein acquiring the ultrasound data includes using a single scanner configured to transmit ultrasound signals at the two locations simultaneously.

* * * * *